(12) United States Patent
Nishida et al.

(10) Patent No.: US 11,357,798 B2
(45) Date of Patent: Jun. 14, 2022

(54) MESENCHYMAL STEM CELL-DERIVED EXOSOME

(71) Applicants: OSAKA UNIVERSITY, Suita (JP); ROHTO PHARMACEUTICAL CO., LTD., Osaka (JP)

(72) Inventors: Kohji Nishida, Suita (JP); Ryuuhei Hayashi, Suita (JP); Yoichi Honma, Osaka (JP); Toru Okubo, Osaka (JP); Shun Shibata, Osaka (JP)

(73) Assignees: OSAKA UNIVERSITY, Osaka (JP); ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/749,766

(22) PCT Filed: Aug. 3, 2016

(86) PCT No.: PCT/JP2016/072855
§ 371 (c)(1),
(2) Date: Feb. 1, 2018

(87) PCT Pub. No.: WO2017/022809
PCT Pub. Date: Feb. 9, 2017

(65) Prior Publication Data
US 2019/0015452 A1     Jan. 17, 2019

(30) Foreign Application Priority Data
Aug. 3, 2015 (JP) .............................. JP2015-153412

(51) Int. Cl.
*A61K 35/28* (2015.01)
*A61P 27/02* (2006.01)
(Continued)

(52) U.S. Cl.
CPC .............. *A61K 35/28* (2013.01); *A61K 35/12* (2013.01); *A61P 27/02* (2018.01); *C12N 5/0012* (2013.01); *C12N 5/0663* (2013.01); *C12Q 1/02* (2013.01)

(58) Field of Classification Search
None
See application file for complete search history.

(56) References Cited

U.S. PATENT DOCUMENTS

| | | | |
|---|---|---|---|
| 9,446,075 B2 * | 9/2016 | Maguire | ................ A61K 35/12 |
| 2010/0184221 A1 | 7/2010 | Yokoo et al. | |

(Continued)

FOREIGN PATENT DOCUMENTS

| | | | |
|---|---|---|---|
| CN | 103767985 A | * | 5/2014 |
| JP | 2011-513217 | | 4/2011 |

(Continued)

OTHER PUBLICATIONS

Baglio, Serena; et al.; "Mesenchymal stem cell secreted vesicles provide novel opportunities in (stem) cell-free therapy" Frontiers in Physiology, 3, 359, 2012 (Year: 2012).*

(Continued)

*Primary Examiner* — David W Berke-Schlessel
(74) *Attorney, Agent, or Firm* — Lewis Roca Rothgerber Christie LLP

(57) ABSTRACT

The present invention relates to mesenchymal stem cell-derived microparticles having activity that promotes the growth of corneal epithelial stem cells and/or corneal epithelial cells, activity that maintains corneal epithelial stem cells in an undifferentiated state or promotes the formation of colonies thereby, and function that protects corneal epithelium.

17 Claims, 5 Drawing Sheets

(51) Int. Cl.
*C12N 5/0775* (2010.01)
*C12N 5/00* (2006.01)
*C12Q 1/02* (2006.01)
*A61K 35/12* (2015.01)

(56) References Cited

U.S. PATENT DOCUMENTS

| | | |
|---|---|---|
| 2011/0003008 A1 | 1/2011 | Lim |
| 2013/0195899 A1 | 8/2013 | Ichim et al. |
| 2013/0209528 A1 | 8/2013 | Levi et al. |
| 2014/0127803 A1 | 5/2014 | Hayashi et al. |
| 2015/0024011 A1 | 1/2015 | Lim et al. |
| 2015/0079046 A1 | 3/2015 | Sinden et al. |
| 2015/0164955 A1 | 6/2015 | Sinden et al. |
| 2015/0190430 A1 | 7/2015 | Lim |
| 2015/0366897 A1 | 12/2015 | Stevanato et al. |
| 2016/0002597 A1 | 1/2016 | Sinden et al. |
| 2016/0008408 A1 | 1/2016 | Imagawa et al. |
| 2017/0189449 A1 | 7/2017 | Lim |

FOREIGN PATENT DOCUMENTS

| | | |
|---|---|---|
| JP | 2013-540150 | 10/2013 |
| JP | 2015-513906 | 5/2015 |
| WO | WO 2005/035739 A1 | 4/2005 |
| WO | WO 2009/011139 A1 | 1/2009 |
| WO | WO 2009/105044 A1 | 8/2009 |
| WO | WO 2012/144582 A1 | 10/2012 |
| WO | WO 2014/142038 A1 | 9/2014 |

OTHER PUBLICATIONS

Ritter, Thomas; et al; "Mesenchymal stem cell-derived extracellular vesicles promote corneal wound repair" Investigative Ophthalmology and Visual Science, 56, 2015 (Year: 2015).*

Yu, Bo; et al; "Exosomes Derived from Mesenchymal Stem Cells" International Journal of Molecular Science, 15, 4142-4157, 2014 (Year: 2014).*

Lai, Ruenn Chai; et al; "Proteolytic Potential of the MSC Exosome Proteome: Implications for an Exosome-Mediated Delivery of Therapeutic Proteasome" International Journal of Proteomics, 2012, 1-14, 2012 (Year: 2012).*

International Search Report, dated Oct. 25, 2016, corresponding to PCT/JP2016/072855, 4 pages.

Yokoyama, et al., "Isolation and comparison of exosomes derived from mesenchymal stem cells and liver cancer cells", 95th Annual Meeting of the Chemical Society of Japan in Spring (2015) Koen Yokoshu II, Mar. 11, 2015 (Mar. 11, 2015), p. 535, 1BP-058, English Abstract.

Raposo, et al., "Extracellular vesicles: Exosomes, microvesicles, and friends", J. Cell Biol. vol. 200 No. 4, pp. 373-383.

Zhou, et al., "ROCK Inhibitor Y-27632 Increases the Cloning Efficiency of Limbal Stem/Progenitor Cells by Improving Their Adherence and ROS-Scavenging Capacity", Tissue Engineering: Part C, vol. 19, No. 7, 2013, pp. 531-537.

Park, et al., "The Side Population Cells in the Rabbit Limbus Sensitively Increased in Response to the Central Cornea Wounding", Invest. Ophthalmol. Vis. Sci., vol. 47, No. 3, 2006, pp. 892-900.

Zhou, et al., "Ciliary Neurotrophic Factor Promotes the Activation of Corneal Epithelial Stem/Progenitor Cells and Accelerates Corneal Epithelial Wound Healing", Stem Cells, 33, 2014, pp. 1566-1576.

Extended European Search Report dated Apr. 5, 2019, issued in corresponding Appln No. 16833088.4, 12 pages.

Zhang, Bin et al., "Mesenchymal Stem Cells Secrete Immunologically Active Exosomes", Stem Cells and Development, vol. 23, No. 11, 2014, pp. 1233-1244, XP055419485.

Joe, Aaron W. et al., "Mesenchymal Stem Cells and Potential Applications in Treating Ocular Disease", Current Eye Research, vol. 35, No. 11, 2010, pp. 941-952, XP05571942.

Yu, Bo et al., "Exosomes Derived from Mesenchymal Stem Cells", International Journal of Molecular Sciences, vol. 15, No. 3, 2014, pp. 4142-4157. XP055407121.

Zhang, Liyun et al., "Mesenchymal stem cells for treating ocular surface diseases", BMC Ophthalmology, vol. 15, Suppl 1, 2015, p. 155, XP002789937.

Daniels, Julie T. et al., "Corneal Epithelial Stem Cells in Health and Disease", Stem Cell Reviews, vol. 2, No. 3, 2006, pp. 247-254, XP055571970.

Vlassov, Alexander V. et al., "Exosomes: Current knowledge of their composition, biological functions, and diagnostic and therapeutic potentials", Biochimica et Biophysica Acta (BBA)-General Subjects, vol. 1820, No. 7, 2012, pp. 940-948, XP055570958.

Jin, Hye Jin et al., "Comparative Analysis of Human Mesenchymal Stem Cells from Bone Marrow, Adipose Tissue, and Umbilical Cord Blood as Sources of Cell Therapy", Int. J. Mol. Sci., 2013, vol. 14, pp. 17986-18001.

Del Fattore, Andrea et al., "Differential effects of extracellular vesicles secreted by mesenchymal stem cells from different sources on glioblastoma cells", Expert Opin. Biol. Ther. (2015) 15(4):495-504.

Katsuda, Takeshi, et al., "Human adipose tissue-derived mesenchymal stem cells secrete functional neprilysin-bound exosomes", Scientific Reports 3:1197, DOI: 10.1038/srep 01197, 11 pages.

Wang, Zheng-gang et al., "Comprehensive proteomic analysis of exosomes derived from human bone marrow, adipose tissue, and umbilical cord mesenchymal stem cells", Stem Cell Research & Therapy (2020) 11:511, 11 pages.

Chinese Office Action dated Jul. 5, 2021 issued in corresponding Chinese Patent Application No. 201680045165.8 and English translation, 15 pages.

Shabbir, Arsalan et al., "Mesenchymal Stem Cell Exosomes Induce Proliferation and Migration of Normal and Chronic Wound Fibroblasts, and Enhance Angiogenesis In Vitro," Stem Cells and Development, 2015, vol. 24, No. 14, p. 1635-1647.

* cited by examiner

[Figure 1]
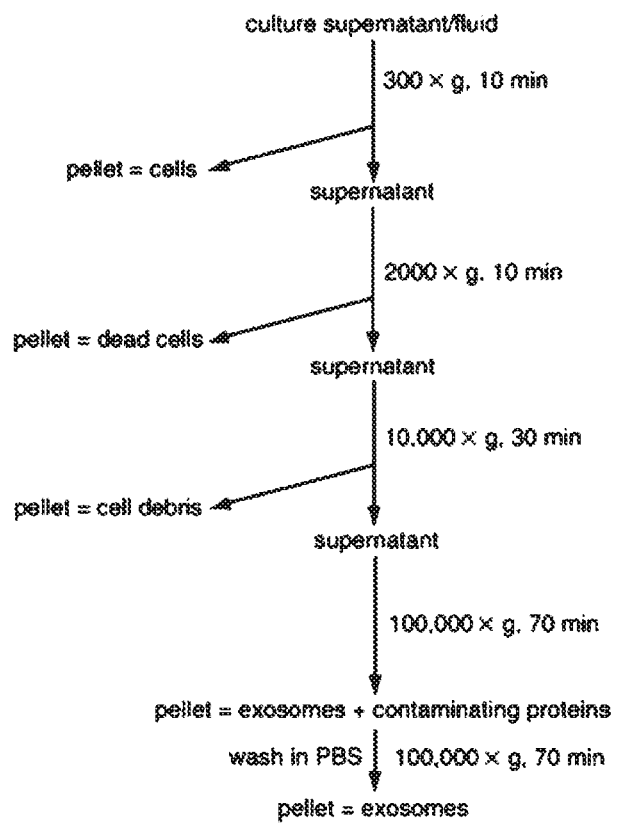

[Figure 2]
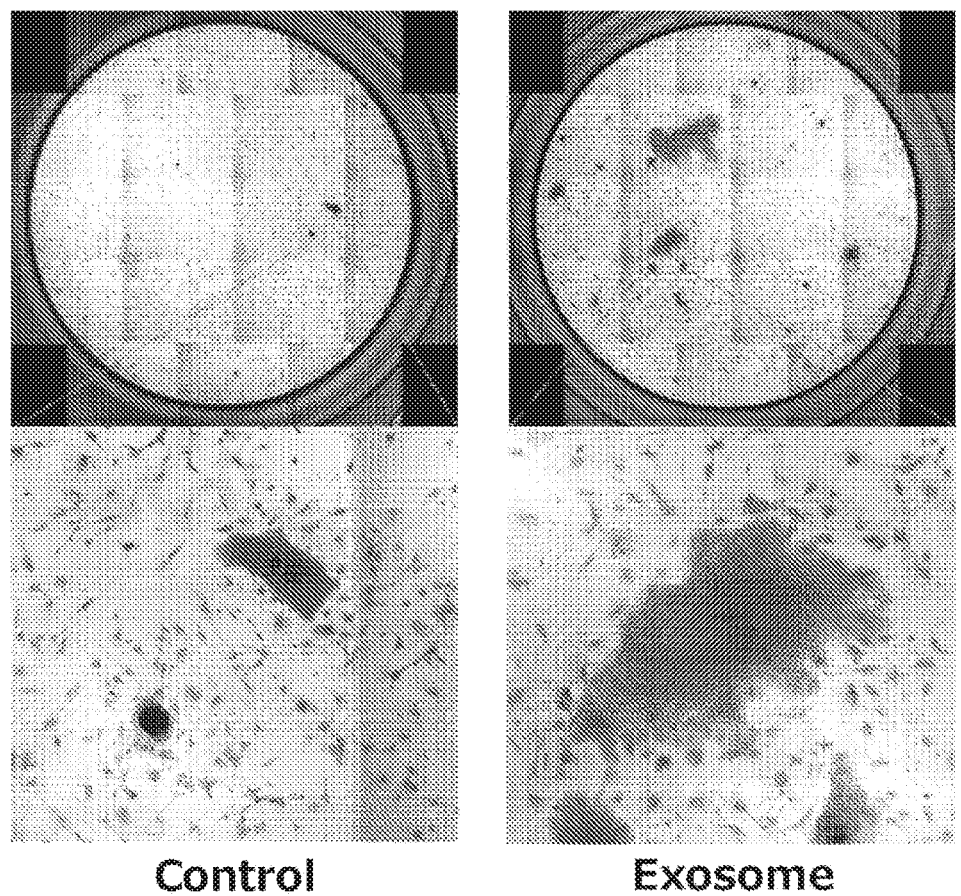
Control          Exosome
[Figure 3]
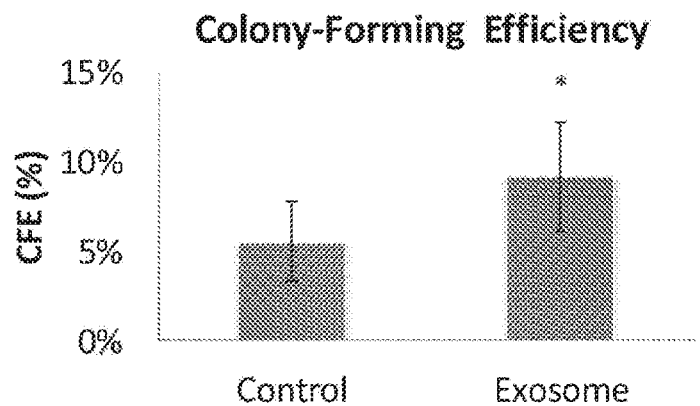

[Figure 4]
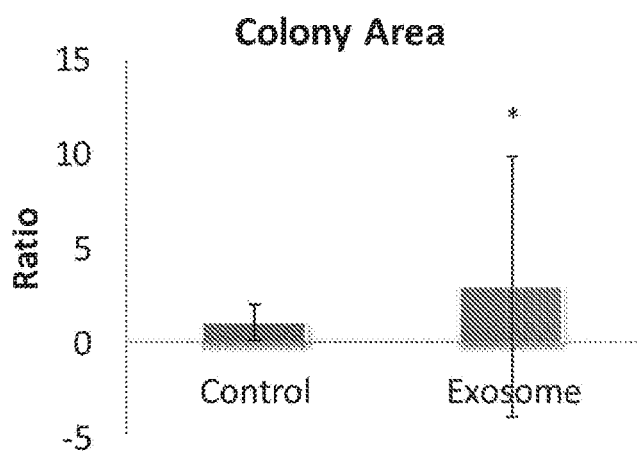

[Figure 5]
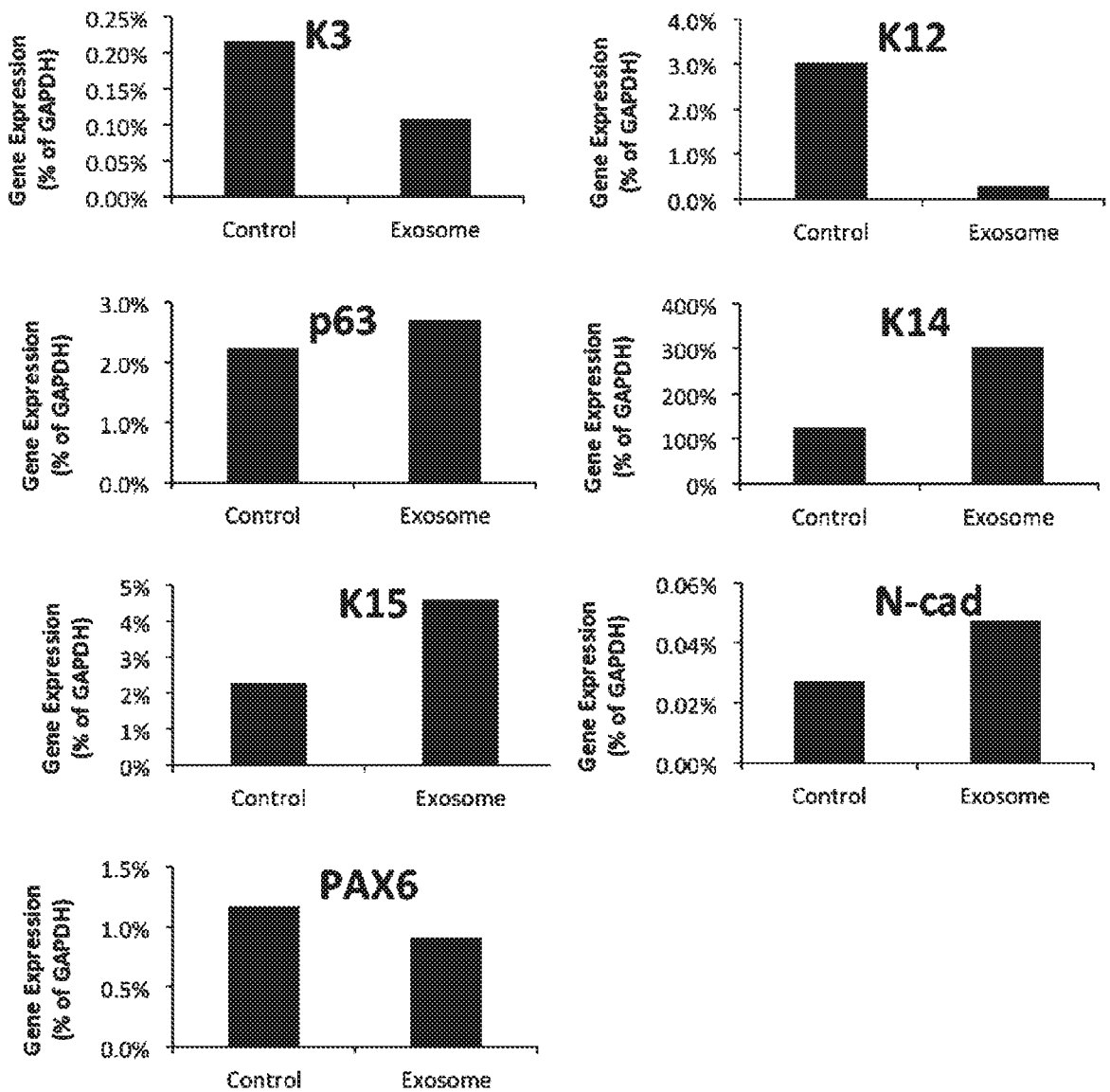

[Figure 6]
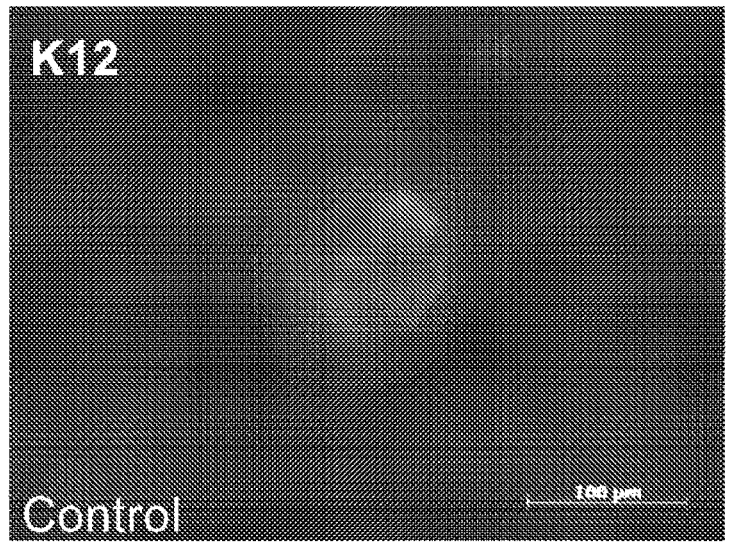
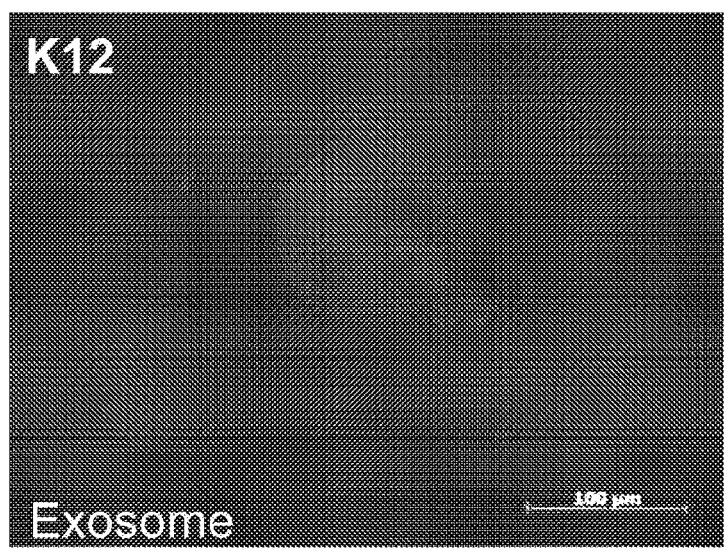

MESENCHYMAL STEM CELL-DERIVED EXOSOME

CROSS-REFERENCE TO RELATED APPLICATION(S)

This application is a National Phase Patent Application and claims priority to and the benefit of International Application Number PCT/JP2016/072855, filed on Aug. 3, 2016, which claims priority to and the benefit of Japanese Patent Application Number 2015-153412, filed on Aug. 3, 2015, the entire contents of all of which are incorporated herein by reference.

TECHNICAL FIELD

The present invention relates to mesenchymal stem cell-derived microparticles having activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium.

BACKGROUND ART

Corneal epithelial stem cells are present in the limbus between the cornea and conjunctiva, and play an important role in the cause and course of treatment of corneal epithelial stem cell deficiency, corneal epithelial disorders and diabetic keratopathy. Although examples of conventional treatment methods for these diseases include the administration of artificial lacrimal fluid, instillation of antibiotics and corneal transplant, there have been problems such as the existence of cases in which ophthalmic solutions are ineffective and allogenic corneal transplants have the risk of rejection along with a shortage of donors.

A method has been reported that consists of inducing iPS cells derived from ocular epidermal cells to differentiate into corneal epithelial cells and corneal epithelial stem cells (Patent Document 1). However, corneal epithelial cells and corneal epithelial stem cells differentiated from iPS cells are still in the process of being developed for clinical application.

Corneal epithelial stem cells are known to form colonies by co-culturing using NIH/3T3 cells as feeder cells. In addition, known examples of markers of corneal epithelial stem cells include K14 (keratin 14), K15 (keratin 15), p63 and N-cadherin. On the other hand, known examples of markers of differentiated corneal epithelial cells include ocular tissue-specific markers (such as pax6) and corneal epithelium-specific markers (such as K3 (keratin 3) or K12 (keratin 12)).

On the other hand, exosomes are vesicles having a diameter of about 30 nm to 150 nm formed with a lipid bilayer membrane that are secreted from various cells. In recent years, tetraspanins (such as CD63, CD81 or CD9) have been determined to be present in the membrane of exosomes, and have been clearly shown to also contain various proteins, mRNA and miRNA. In addition, exosomes have been reported to be able to be obtained from, for example, cell culture supernatant by ultracentrifugation (Non-Patent Document 1).

Mesenchymal stem cells (MSC) are lineage-restricted stem cells that have the potential to differentiate only into mesenchymal cell types, namely adipocyte cell lines, chondrocyte cell lines and osteocyte cell lines. Mesenchymal stem cells are derived from various sources such as bone marrow, blood, fat and other somatic tissue.

Patent Document 2 describes that exosomes of mesenchymal stem cells derived from embryonic stem cells can be used for therapeutic means including the a cardioprotective effect.

In addition, Patent Document 3 describes that exosomes derived from neural stem cells are effective in healing wounds and stimulating vascularization and neurite outgrowth.

Corneal epithelial diseases are diseases in which the corneal epithelium has been damaged by some cause, and examples of causes of corneal epithelial stem cell deficiency, for example, include congenital factors such as aniridia or sclerocornea, extrinsic factors such as alkali corrosion or burns, intrinsic factors such as Stevens-Johnson syndrome or ocular pemphigoid, and other idiopathic factors.

Moreover, although research on therapeutic drugs for diseases such as corneal epithelial stem cell deficiency has recently been conducted focusing on the colony formation promoting action of corneal epithelial stem cells, exosomes have not been reported to have function that promotes colony formation by corneal epithelial stem cells (Non-Patent Documents 2 to 4).

PRIOR ART DOCUMENTS

Patent Documents

Patent Document 1: WO 2012/144582
Patent Document 2: JP-T 2011-513217
Patent Document 3: JP-T 2015-513906

Non-Patent Documents

Non-Patent Document 1: Graca Raposo and Willem Stoorvogel, J. Cell Biol., Vol. 200, No. 4, 373-383
Non-Patent Document 2: Zhou, Q., et al., Tissue Eng. Part C Methods, 2013 July, 19(7), 531-7
Non-Patent Document 3: Park, K., et al., Invest. Ophthalmol. Vis. Sci., 2006, 47(3), 892-900
Non-Patent Document 4: Zhou, Q., et al., Stem Cells (Dayton, Ohio), 33(5), 1566-76

DISCLOSURE OF THE INVENTION

Problems to be Solved by the Invention

An object of the present invention is to provide mesenchymal stem cell-derived microparticles that are useful in the prevention and/or treatment of corneal epithelial diseases, and has activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium.

Means for Solving the Problems

As a result of conducting extensive research to solve the aforementioned problems, the inventors of the present invention found that mesenchymal stem cell-derived microparticles have activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium, thereby leading to completion of the present invention.

The present invention relates to that indicated below.

1. Mesenchymal stem cell-derived microparticles having activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium.

2. The mesenchymal stem cell-derived microparticles described in 1, wherein the mesenchymal stem cell-derived microparticles have a density as determined by density gradient centrifugation of 1.13 g/mL to 1.19 g/mL.

3. The mesenchymal stem cell-derived microparticles described in 1 or 2, wherein the mesenchymal stem cell-derived microparticles are exosomes.

4. A growth promoter of corneal epithelial stem cells and/or corneal epithelial cells, an undifferentiated corneal epithelial cell maintenance agent or corneal epithelial cell colony formation promoter, or a corneal epithelium protective agent containing mesenchymal stem cell-derived microparticles as an active ingredient thereof.

5. A preventive or therapeutic agent for corneal epithelial diseases containing mesenchymal stem cell-derived microparticles as an active ingredient thereof.

6. The preventive or therapeutic agent for corneal epithelial diseases described in 5, wherein the corneal epithelial disease is selected from the group consisting of heat corrosion, alkali corrosion, acid corrosion, chemical toxicity, Stevens-Johnson syndrome, ocular pemphigoid, (recurrent) pterygium, persistent corneal epithelial defect, corneal puncture, corneal marginal ulcer, corneal ulcer, epithelial detachment following excimer laser surgery, radiation keratopathy, aniridia, post-trachoma corneal opacification, Salzmann's corneal degeneration, corneal erosion, symblepharon, cryptogenic diseases associated with loss of corneal epithelial stem cells, limbus tumor, graft versus host disease (GVHD), keratitis, superficial punctate keratopathy, dry eye, keratoconjunctivitis sicca, corneal epithelial stem cell deficiency, corneal dystrophy, diabetic keratopathy and corneal epithelial disorders.

7. The preventive or therapeutic agent for corneal epithelial diseases described in 5, wherein the corneal epithelial disease is selected from the group consisting of corneal epithelial disorders, superficial punctate keratopathy, corneal erosion, corneal marginal ulcer, persistent corneal epithelial defect, dry eye, epithelial detachment following excimer laser surgery, heat corrosion, alkali corrosion, acid corrosion, chemical toxicity, diabetic keratopathy, corneal epithelial stem cell deficiency, Stevens-Johnson syndrome, ocular pemphigoid, aniridia, cryptogenic diseases associated with loss of corneal epithelial stem cells and graft versus host disease (GVHD).

8. The preventive or therapeutic agent for corneal epithelial diseases described in 5, wherein the corneal epithelial disease is selected from the group consisting of corneal epithelial disorders, superficial punctate keratopathy, corneal erosion, corneal marginal ulcer, persistent corneal epithelial defect, dry eye, epithelial detachment following excimer laser surgery, heat corrosion, alkali corrosion, acid corrosion, chemical toxicity and diabetic keratopathy.

9. The preventive or therapeutic agent for corneal epithelial diseases described in 8, wherein the corneal epithelial stem cell deficiency is caused by an extrinsic factor, an intrinsic factor, a congenital defect or a neoplastic disease.

10. A method for culturing corneal epithelial stem cells that includes culturing in the presence of mesenchymal stem cell-derived microparticles.

11. Corneal epithelial stem cells and/or corneal epithelial cells obtained according to the culture method described in 10.

12. A method for screening preventive or therapeutic agents for corneal epithelial diseases that uses colony formation by corneal epithelial stem cells as an indicator.

The present invention also relates to that indicated below.

13. A composition containing an effective amount of mesenchymal stem cell-derived microparticles for promoting the growth of corneal epithelial stem cells and/or corneal epithelial cells, maintaining corneal epithelial stem cells in an undifferentiated state or promoting the formation of colonies by corneal epithelial stem cells, or protecting corneal epithelium.

14. A pharmaceutical composition for preventing or treating corneal epithelial diseases containing a therapeutically effective amount of mesenchymal stem cell-derived microparticles.

15. A use of mesenchymal stem cell-derived microparticles in a method for promoting the growth of corneal epithelial stem cells and/or corneal epithelial cells, maintaining corneal epithelial stem cells in an undifferentiated state or promoting the formation of colonies by corneal epithelial stem cells, or protecting corneal epithelium.

16. A use of mesenchymal stem cell-derived microparticles in a method for preventing or treating corneal epithelial diseases.

17. A use of mesenchymal stem cell-derived microparticles in the production of a composition that promotes the growth of corneal epithelial stem cells and/or corneal epithelial cells, maintains corneal epithelial stem cells in an undifferentiated state or promotes the formation of colonies by corneal epithelial stem cells, or protects corneal epithelium.

18. A use of mesenchymal stem cell-derived microparticles in the production of a pharmaceutical for preventing or treating corneal epithelial diseases.

19. A method for promoting the growth of corneal epithelial stem cells and/or corneal epithelial cells, maintaining corneal epithelial stem cells in an undifferentiated state or promoting the formation of colonies by corneal epithelial stem cells, or protecting corneal epithelium that includes administering an effective amount of a mesenchymal stem cell-derived microparticles.

20. A method for preventing or treating corneal epithelial diseases that includes administering a therapeutically effective amount of mesenchymal stem cell-derived microparticles.

21. Furthermore, each of the configurations of 1 to 20 can be combined by arbitrarily selecting two or more configurations.

Effects of the Invention

According to the mesenchymal stem cell-derived microparticles of the present invention, the growth of corneal epithelial stem cells and/or corneal epithelial cells can be promoted, activity that maintains corneal epithelial stem cells in an undifferentiated state or activity that promotes the formation of colonies by corneal epithelial stem cells can be increased, or corneal epithelium can be protected in patients with various corneal epithelial diseases. Consequently, the mesenchymal stem cell-derived microparticles of the present invention can be used to prevent and/or treat various corneal epithelial diseases.

BRIEF DESCRIPTION OF THE DRAWINGS

FIG. 1 is a flow chart indicating conditions for separating the mesenchymal stem cell-derived microparticles of the present invention.

FIG. 2 depicts photographs showing the colony formation promoting action of the mesenchymal stem cell-derived microparticles of the present invention.

FIG. 3 is a indicating the colony formation promoting action (based on the number of colonies) of the mesenchymal stem cell-derived microparticles of the present invention.

FIG. 4 is a graph indicating the colony formation promoting action (based on colony size) of the mesenchymal stem cell-derived microparticles of the present invention.

FIG. 5 depicts graphs indicating the undifferentiated maintenance activity of the mesenchymal stem cell-derived microparticles of the present invention.

FIG. 6 depicts micrographs indicating suppression of the expression of K12 by the mesenchymal stem cell-derived microparticles of the present invention.

BEST MODE FOR CARRYING OUT THE INVENTION

The following provides an explanation of the mesenchymal stem cell-derived microparticles of the present invention.

<Mesenchymal Stem Cells>

Examples of mesenchymal stem cells in the present invention include mesenchymal stem cells derived from bone marrow, fat, muscle, nerves, skin, amnion, placenta, chorionic membrane, decidua and umbilical cord, preferably include those derived from bone marrow, fat and placenta, and more preferably fat-derived mesenchymal stem cells.

Mesenchymal stem cells in the present invention may be characterized by growth characteristics (such as population doubling capacity or doubling time from subculturing to aging), karyotype analysis (such as normal karyotype, maternal lineage or neonatal lineage), expression of surface markers as determined by flow cytometry (such as FACS analysis), immunohistochemistry and/or immunocytochemistry (such as epitope detection), gene expression profiling (such as a gene chip array or polymerase chain reaction in the manner of reverse transcription PCR, real-time PCR or conventional PCR), miRNA expression profiling, protein array, cytokine and other protein secretion (such as plasma coagulation analysis, ELISA or cytokine array), metabolites (such as metabolome analysis), or other methods known in the art.

<Culturing of Mesenchymal Stem Cells>

The mesenchymal stem cells in the present invention can be cultured by, for example, the method indicated below. Namely, mesenchymal stem cells such as tissue-derived mesenchymal stem cells or established mesenchymal stem cells can be cultured in conditioned medium followed by culturing the mesenchymal stem cells in non-conditioned medium.

Media conventionally known among persons with ordinary skill in the art can be respectively used for the aforementioned conditioned medium for each type of mesenchymal stem cell, and there are no particular limitations thereon. Examples of conditioned media include mesenchymal stem cell culture media available from PromoCell GmbH, Lifeline Cell Technology, LLC, or Lonza Group Ltd. Although the conditioned medium may contain biological raw materials (such as animal serum), when considering that the resulting cells and culture supernatants thereof are used to treat diseases of animals (including humans), medium not containing biological raw materials (such as serum-free medium) is preferably used whenever possible.

Non-conditioned medium refers to medium used after cells have adequately been conditioned, and may be a medium having the same composition as conditioned medium or a medium having a different composition. There are no particular limitations on the non-conditioned medium provided it is suitable for culturing the mesenchymal stem cells in the present invention. Media respectively selected for each type of mesenchymal stem cell can be used for the aforementioned non-conditioned medium, and examples of media that can be used include media normally used to culture mesenchymal stem cells, media normally used to culture cells other than mesenchymal stem cells, media obtained by removing specific components from conditioned media, and media obtained by adding specific components to conditioned media. Although it is preferable to use media not containing as much as possible biological raw materials for the non-conditioned medium when considering that the resulting microparticle is used to treat diseases of animals (including humans), biological raw materials such as albumin or FCS can be added as necessary. Examples thereof include MSCGM-CD medium and medium containing FCS within a range of 0.1% to 10% in this or other basal media.

The aforementioned serum-free medium is only required to be a medium that does not contain animal serum as an additive thereof, and there are no particular limitations thereon. Media having a composition containing other additives except for animal serum in a known basal medium can be used for the serum-free medium. The composition of the basal medium can be suitably selected according to the type of cells to be cultured. Examples thereof include minimum essential medium (MEM) in the manner of Eagle's medium, Dulbecco's modified Eagle's medium (DMEM), minimum essential medium α (MEM-α), mesenchymal stem cell basal medium (MSCBM), Ham's F-12 and F-10 medium, DMEM/F12 medium, Williams' medium E, RPMI-1640 medium, MCDB medium, 199 medium, Fisher's medium, Iscove's modified Dulbecco's medium (IMDM) and McCoy's modified medium.

Examples of other additives added to the basal medium include amino acids, inorganic salts, vitamins, carbon sources, antibiotics and other additives. There are no particular limitations on the concentrations at which these additives are used, and can be used at a concentration normally used in mammalian cell media.

Examples of amino acids include glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine and L-valine.

Examples of inorganic salts include calcium chloride, copper sulfate, iron (III) nitrate, iron sulfate, magnesium chloride, magnesium sulfate, potassium chloride, sodium bicarbonate, sodium chloride, disodium hydrogen phosphate and sodium dihydrogen phosphate.

Examples of vitamins include choline, vitamin A, vitamin B1, vitamin B2, vitamin B3, vitamin B4, vitamin B5, vitamin B6, vitamin B7, vitamin B12, vitamin B13, vitamin B15, vitamin B17, vitamin Bh, vitamin Bt, vitamin Bx, vitamin C, vitamin D, vitamin E, vitamin F, vitamin K, vitamin M and vitamin P.

Examples of other additives include growth factors such as fibroblast growth factor (FGF), endothelial cell growth factor (EGF), platelet-derived growth factor (PDGF), epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte colony-stimulating factor (G-C SF), granulocyte-macrophage colony-stimulating factor (GM-CSF), erythropoietin (EPO), thrombopoietin (TPO) or hepatocyte growth factor (HGF), antibiotics such as penicillin, streptomycin, gentamycin or kanamycin, carbon sources such as glucose, galactose, fructose or sucrose, trace metals such as magnesium, iron, zinc, calcium, potassium, sodium, copper, selenium, cobalt, tin, molybdenum, nickel or silicon, stem cell differentiation-inducing agents such as β-glycerophosphoric acid, dexamethasone, rosiglitazone, isobutyl methylxanthine or 5-azacytidine, antioxidants such as 2-mercaptoethanol, catalase, superoxide dismutase or N-acetylcysteine, adenosine 5'-phosphate, corticosterone, ethanolamine, insulin, reduced glutathione, lipoic acid, melatonin, hypoxanthine, phenol red, progesterone, putrescine, pyruvic acid, thymidine, triiodothyronine, transferrin, lactoferrin, albumin, Wnt signaling activators, ROCK inhibitors, growth factors, steroidal compounds, PTEN inhibitors, p53 inhibitors and p38 inhibitors.

An example of a serum-free medium preferable for the mesenchymal stem cells in the present invention is a commercially available serum-free medium. This serum-free medium may further contain components selected from antioxidants, animal serum albumin, growth factors, surfactants, Edg ligands, serotonin ligands, Wnt signaling activators, ROCK inhibitors, growth factors, steroidal compounds, PTEN inhibitors, p53 inhibitors and p38 inhibitors.

There are no particular limitations on the culturing conditions of the mesenchymal stem cells in the present invention provided they are each suitable for mesenchymal stem cells, and conditions similar to those used in conventional methods are used. Normally, culturing is carried out at a temperature of 30° C. to 37° C. in an environment containing 2% to 7% $CO_2$ and 5% to 21% $O_2$. In addition, there are also no particular limitations on the timing and method used to subculture the mesenchymal stem cells provided they are each suitable for the cells, and those similar to the prior art can be used while monitoring the status of the cells.

<Mesenchymal Stem Cell-Derived Microparticle>

The mesenchymal stem cell-derived microparticles of the present invention are microparticles obtained from a mesenchymal stem cell. Mesenchymal stem cell-derived microparticles are microparticles produced by mesenchymal stem cells. The microparticles are typically secreted from mesenchymal stem cells.

The mesenchymal stem cell-derived microparticles of the present invention are vesicles that are released from mesenchymal stem cells and can be confirmed with an electron microscope. The mesenchymal stem cell microparticle can have a lipid bilayer surrounding biomolecules. The mesenchymal stem cell microparticle includes, for example, membrane particles, membrane vesicles, microvesicles, exosome-like vesicles, exosomes, ectosome-like vesicles, ectosomes or exovesicles. Different types of mesenchymal stem cell microparticles are distinguished on the basis of diameter, intracellular origin, microparticle density in sucrose, morphology, sedimentation rate, lipid composition, protein markers and form of secretion (namely, after a signal (by being induced) or spontaneously (based on composition)). Exosomes are fractionated at 1.13 g/mL to 1.19 g/mL by density gradient centrifugation, for example, and the particle diameter thereof can be measured by dynamic light scattering and the like.

The mesenchymal stem cell-derived microparticles of the present invention contain, for example, CD9, CD63, CD81, GAPDH, PKM, enolase-1, 40S ribosomal protein S2, S5, SA, S13, S23, S4, S16 and S9, 60S acidic ribosomal protein PO and P1, 60S ribosomal protein L9, HSPB1 and HSP7C, 14-3-3 protein zeta/delta, epsilon, theta, beta/alpha, gamma and eta, syntenin, TGS101, actin cytoplasmic-1, cofilin-1, annexin A1, A2, A5, A6, A7 and A11, Rab-1B, 7a, 8B, 11A, 13 and 35, ICAM-1, integrin alpha-V, alpha-2, alpha-4, alpha-5, beta-1 and beta-5, MMP-14, brain acid-soluble protein 1, lysyl oxidase, Rap-2c and catenin β-1.

<Recovery of Mesenchymal Stem Cell-Derived Microparticle>

The mesenchymal stem cell-derived microparticles of the present invention can be recovered by carrying out expansion culturing on the mesenchymal stem cells in conditioned medium to subconfluency (or confluency), replacing the medium with fresh conditioned medium, culturing for normally 1 to 5 days (e.g., 1 day, 2 to 3 days or 3 to 4 days) and recovering the microparticle from the culture supernatant.

Examples of methods used to recover the mesenchymal stem cell-derived microparticles of the present invention include ultracentrifugation, density gradient centrifugation and the use of various types of exosome separation kits (such as the formation of a pellet by centrifugation, immunoprecipitation, purification with magnetic beads, fractionation according to particle size or column adsorption).

The method used to recover the mesenchymal stem cell-derived microparticles of the present invention includes subjecting a culture supernatant of mesenchymal stem cells to ultracentrifugation for 0.5 hours to 2 hours at about 50,000 G to 150,000 G The method can also include centrifuging the culture supernatant of the mesenchymal stem cells to 0.1 hours to 2 hours at about 100 G to 20,000 G prior to carrying out ultracentrifugation. The mesenchymal stem cell-derived microparticles of the present invention can be stored for about 1 week at 4° C., for about 1 month at −20° C. or for about 6 months at −80° C. provided it is stored dissolved in a solution such as PBS, and can be stored for about 3 years at 4° C. provided it has been freeze-dried.

The mesenchymal stem cell-derived microparticles of the present invention have activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium.

<Corneal Epithelial Stem Cells>

Corneal epithelial stem cells have the ability to proliferate (ability to remain undifferentiated or form colonies) and express markers specific to corneal epithelial stem cells. Corneal epithelial stem cells are able to differentiate into corneal epithelial cells. Corneal epithelial cells and/or corneal epithelial stem cells are present in the limbus between the cornea and conjunctiva.

<Evaluation of Mesenchymal Stem Cell-Derived Microparticles>

The mesenchymal stem cell-derived microparticles of the present invention can be evaluated for the activity that promotes the growth of corneal epithelial stem cells and/or corneal epithelial cells, the activity that maintains corneal epithelial stem cells in an undifferentiated state or promotes the formation of colonies by corneal epithelium stem cells, and the action that protects corneal epithelium thereof using means known among persons with ordinary skill in the art.

In the present invention, activity that promotes growth, or "growth promoting activity", refers to the promotion of cell growth, and in the case of corneal epithelial stem cells, for example, can be confirmed by measuring the number and size of colonies by inducing the formation of colonies during subculturing, while in the case of corneal epithelial cells, includes promoting the growth of corneal epithelial stem cells followed by differentiation of the corneal epithelial stem cells into corneal epithelial cells.

In the present invention, the ability to promote the formation of colonies, or "colony formation promoting activity", refers to allowing cultured cells to proliferate and promoting the formation of colonies, and in the case of corneal epithelial stem cells, for example, can be confirmed by measuring the number and size of colonies by inducing the formation of colonies during subculturing.

In the present invention, activity that maintains a differentiated state, or "undifferentiated cell maintenance activity", refers to maintaining cultured cells in an undifferentiated state, and in the case of corneal epithelial stem cells, for example, refers to maintaining the cells in an undifferentiated state, and whether or not corneal epithelial stem cells have differentiated during culturing can be evaluated by measuring a marker such as K14 (keratin 14), K15 (keratin 15) and/or p63 and/or N-cadherin.

In the present invention, the "action that protects corneal epithelium" refers to a corneal epithelium protecting action, and enables corneal epithelium to be protected by replenishing corneal epithelial stem cells and/or corneal epithelial cells that have decreased or are no longer present due to some cause by allowing the corneal epithelial stem cells and/or corneal epithelial cells to proliferate.

<Promotion of Proliferative Capacity of Corneal Epithelial Stem Cells by Mesenchymal Stem Cell-Derived Microparticle>

The proliferative capacity of corneal epithelial stem cells can be evaluated by, for example, disseminating corneal epithelial stem cells in a culture system in the presence of the mesenchymal stem cell-derived microparticles of the present invention and subculturing the cells followed by confirming the growth of the corneal epithelial stem cells, although not limited thereto. Growth of the corneal epithelial stem cells can be confirmed by the formation of colonies during subculturing. Although subculturing for the purpose of confirming the formation of colonies is preferably carried out by co-culturing with feeder cells (such as NIH/3T3 cells) or carried out in medium for epithelial cells or epithelial stem cells, the subculturing is not limited thereto. The aforementioned proliferative capacity is preferably the capacity to self-replicate. There are no particular limitations on the method used to evaluate whether cells have the ability to self-replicate, and an example thereof consists of using as indicators not only the proliferative capacity of cells, but also the absence of any change in the properties of the cells following proliferation as a result of subculturing.

<Corneal Epithelial Stem Cell Markers>

Although corneal epithelial stem cells having the ability to proliferate can be confirmed with the corneal epithelial stem cell markers to be subsequently described, confirmation is not limited thereto.

Evaluation of the expression of markers specific to corneal epithelial stem cells by a cell can be carried out by a method known among persons with ordinary skill in the art. Examples of corneal epithelial stem cell markers include, but are not limited to, markers specific to stratified epithelial stem cells (and progenitor cells) consisting of K14 (keratin 14), K15 (keratin 15) and/or p63 and/or N-cadherin. In addition, ocular tissue-specific markers (such as pax6) and/or corneal epithelium-specific differentiation markers (such as K3 (keratin 3) or K12 (keratin 12)) can also be detected. In addition, cell surface markers specifically expressed by corneal epithelial stem cells (such as integrin alpha 6 or N-cadherin) can also be detected after having detected a corneal epithelium-specific differentiation marker (K12).

<Detection of Corneal Epithelial Stem Cell Markers>

Specific methods are known for detecting the expression of corneal epithelial stem cell markers, and consist of detecting expression of a reporter gene and detecting expression by immunocytochemistry. Expression of a reporter gene following induction of differentiation may also be detected by introducing a reporter gene of the aforementioned corneal epithelial stem cells (such as a reporter gene having a promoter region of a gene encoding a corneal epithelial stem cell marker coupled with a fluorescent protein such as green fluorescent protein (GFP)) into pluripotent stem cells induced to differentiate. Other examples of detection methods include detection by microscopic observation using antibody staining, and detection of cell surface markers by a cell sorter (flow cytometer).

<Culturing of Corneal Epithelial Stem Cells>

The present invention also relates to a method for culturing corneal epithelial stem cells that is characterized by culturing in the presence of mesenchymal stem cell-derived microparticles.

The method for culturing corneal epithelial stem cells of the present invention includes the steps indicated below: (1) a step for culturing corneal epithelial cells harvested from the corneal limbus in the presence of mesenchymal stem cell-derived microparticles, and (2) a step for selecting corneal epithelial stem cells from the cultured cells.

The aforementioned step (1) includes co-culturing of corneal epithelial cells harvested from the limbus of an imported human cornea with NIH/3T3 as feeder cells.

Step (2) includes selecting corneal epithelial stem cells by using as indicators the ability to self-proliferate from the cells (cell population) cultured in step (1) and/or the expression of a marker specific to corneal epithelial stem cells.

Furthermore, corneal epithelial stem cells obtained according to the production method of the present invention may include corneal epithelial progenitor cells. In addition, the aforementioned corneal epithelial cells include corneal epithelial cells and/or corneal epithelial stem cells.

There are no particular limitations on the medium used to culture corneal epithelial stem cells provided the medium allows the culturing of corneal epithelial stem cells (including media known among persons with ordinary skill in the art such as keratinocyte-conditioned medium (KCM medium), keratinocyte serum-free medium (KSFM medium available from Invitrogen Corp.), CnT-20 medium (CELLnTEC Advanced Cell Systems AG) or CnT-50 medium (CELLnTEC Advanced Cell Systems AG). During the aforementioned subculturing, in the case of using, for example, a 12-well plate, the re-seeding density is preferably 2000 cells/well to 16000 cells/well.

<Corneal Epithelial Cell Sheet>

The corneal epithelial cell sheet of the present invention is a corneal epithelial cell sheet derived from corneal epithelial stem cells and/or corneal epithelial progenitor cells obtained according to the culture method of the present invention. The aforementioned corneal epithelial cell sheet may be a multilayered sheet of corneal epithelial cell sheets.

The method used to produce the corneal epithelial cell sheet can be suitably selected using a method known among persons with ordinary skill in the art or a method to be developed in the future.

Although there are no particular limitations thereon, an example of a method used to produce the corneal epithelial cell sheet includes a step for culturing the aforementioned corneal epithelial stem cells in a temperature-responsive culture dish or carrier in the presence of feeder cells, and a step for recovering the cell sheet obtained in the aforementioned step. The method may include culturing the aforementioned corneal epithelial stem cells in the presence of the mesenchymal stem cell-derived microparticles of the present invention depending on the case.

<Pharmaceutical Applications of Mesenchymal Stem Cell-Derived Microparticle>

The present invention also relates to a preventive or therapeutic agent for corneal epithelial diseases containing mesenchymal stem cell-derived microparticles as an active ingredient thereof.

The present invention also relates to a pharmaceutical composition for preventing or treating corneal epithelial diseases containing mesenchymal stem cell-derived microparticles as an active ingredient thereof.

The present invention also relates to a use of mesenchymal stem cell-derived microparticles in the production of a pharmaceutical for preventing and/or treating corneal epithelial diseases.

The present invention also relates to a method for preventing and/or treating corneal epithelial diseases that includes administering a prophylactically and/or therapeutically effective amount of mesenchymal stem cell-derived microparticles to a subject requiring such prevention and/or treatment.

The aforementioned corneal epithelial diseases refer to diseases resulting in damage to the corneal epithelium by some cause, and examples thereof include heat corrosion, alkali corrosion, acid corrosion, chemical toxicity, Stevens-Johnson syndrome, ocular pemphigoid, (recurrent) pterygium, persistent corneal epithelial defect, corneal puncture, corneal marginal ulcer, corneal ulcer, epithelial detachment following excimer laser surgery, radiation keratopathy, aniridia, post-trachoma corneal opacification, Salzmann's corneal degeneration, corneal erosion, symblepharon, cryptogenic diseases associated with loss of corneal epithelial stem cells, limbus tumor, graft versus host disease (GVHD), keratitis, superficial punctate keratopathy, dry eye, keratoconjunctivitis sicca, corneal epithelial stem cell deficiency, corneal dystrophy, diabetic keratopathy and corneal epithelial disorders. Preferable examples of the aforementioned corneal epithelial diseases include corneal epithelial disorders, superficial punctate keratopathy, corneal erosion, corneal marginal ulcer, persistent corneal epithelial defect, dry eye, epithelial detachment following excimer laser surgery, heat corrosion, alkali corrosion, acid corrosion, chemical toxicity, diabetic keratopathy, corneal epithelial stem cell deficiency, Stevens-Johnson syndrome, ocular pemphigoid, aniridia, cryptogenic diseases associated with loss of corneal epithelial stem cells and graft versus host disease (GVHD), while more preferable examples include corneal epithelial disorders, superficial punctate keratopathy, corneal erosion, corneal marginal ulcer, persistent corneal epithelial defect, dry eye, epithelial detachment following excimer laser surgery, heat corrosion, alkali corrosion, acid corrosion, chemical toxicity and diabetic keratopathy. In addition, the aforementioned corneal epithelial stem cell deficiency is caused by extrinsic factors (such as heat, chemical trauma, drug toxicity, etc), intrinsic factors (such as Stevens-Johnson syndrome, ocular pemphigoid or GVHD), congenital defects (such as hypoplasia of the limbus due to developmental abnormalities during the embryonic stage such as aniridia or sclerocornea), or neoplastic diseases (such as stratified squamous cell carcinoma originating in the limbus).

The preventive or therapeutic agent and pharmaceutical composition of the present invention may be administered simultaneously with other pharmaceuticals or may be administered at a suitable time before or after the administration of other pharmaceuticals.

The preventive or therapeutic agent and pharmaceutical composition of the present invention can be formulated into a suitable preparation in accordance with ordinary methods. Although the preparation form may be a solid preparation such as a powder or granules, the preparation form is preferably a liquid such as solution, emulsion or suspension from the viewpoint obtaining superior preventive and/or therapeutic effects. The preparation is more preferably in the form of a solution in the case of using in the form of an ophthalmic solution in particular. Examples of methods used to produce the aforementioned ophthalmic solution include a method consisting of mixing a preliminarily prepared culture supernatant of mesenchymal stem cell-derived microparticles and mesenchymal stem cells with a solvent, and a method consisting of further mixing in a suspending agent or emulsifier. As was previously described, a suitable pharmaceutically acceptable carrier can be optionally incorporated in the preparation of the pharmaceutical composition of the present invention as necessary, examples of which include a vehicle, binder, solvent, solubilizing agent, suspending agent, emulsifier, isotonic agent, buffer, stabilizer, analgesic agent, preservative, antioxidant, colorant, lubricant, disintegrating agent, humectant, adsorbent, sweetener and diluent. Furthermore, if the pharmaceutical composition of the present invention contains cells, ingredients acceptable to the cell preparation can be incorporated.

Although there are no particular limitations on the method used to administer the preventive or therapeutic agent and pharmaceutical composition of the present invention, preferable examples thereof include intravascular administration (and preferably intravenous administration), intraperitoneal administration, intestinal administration, subcutaneous administration and instillation.

Although able to be varied according to such factors as the type of disease, severity of the symptoms thereof, drug form or body weight of the administered subject, the dosage of preparations of the preventive or therapeutic agent and pharmaceutical composition of the present invention can be preferably exemplified to be within a range of 1 pg/kg to 100 mg/kg per day as the amount of mesenchymal stem cell-derived microparticles, and can be more preferably exemplified within a range of 100 pg/kg to 10 mg/kg. Furthermore, administration of the preventive or therapeutic agent and pharmaceutical composition of the present invention may be carried out once per day or divided among multiple administrations per day. In addition, administration of the preventive or therapeutic agent and pharmaceutical composition of the present invention may be in the form of a single administration or continuous administration. In the case of continuous administration, the preventive or therapeutic agent and pharmaceutical composition of the present invention is administered at a frequency of one or more times in 3 days successively carried out 2 or more times, preferably administered at a frequency of one or more times in 2 days successively carried out 3 or more times, and more preferably administered at a frequency of one or more times in 1 day successively carried out 4 or more times.

In the case a preparation of the preventive or therapeutic agent and pharmaceutical composition of the present invention is an ophthalmic solution, the ophthalmic solution can be formulated using technology widely used to prepare ophthalmic solutions along with pharmaceutically acceptable additives as necessary.

The aforementioned ophthalmic solution can be prepared by suitably selecting and using isotonic agents such as sodium chloride or concentrated glycerin, pH adjusters such as hydrochloric acid or sodium hydroxide, buffers such as sodium phosphate or sodium acetate, surfactants such as polyoxyethylene sorbitan monooleate, Polyoxyl 40 stearate or polyoxyethylene hydrogenated castor oil, stabilizers such as sodium citrate or sodium edetate, or preservatives such as benzalkonium chloride or paraben, as necessary. Although the pH of the present ophthalmic solution is only required to be within at range allowable for ophthalmic preparations, normally it is preferably within the range of 4 to 8.

Although there are no particular limitations thereon, examples of animals targeted for administration of a preparation of the preventive or treatment agent and pharmaceutical composition of the present invention preferably include humans, monkeys, mice, rats, hamsters, guinea pigs, cows, pigs, horses, rabbits, sheep, goats, cats and dogs, and more preferably include humans. In addition, when the preventive or therapeutic agent and pharmaceutical composition of the present invention contains cells and/or a supernatant thereof, it is preferable that the preventive or therapeutic agent and pharmaceutical composition of the present invention matches the type of animal targeted for administration of the preventive or therapeutic agent and pharmaceutical composition of the present invention from the viewpoint of obtaining more stable and superior preventive and/or therapeutic effects for disease.

EXAMPLES

Although the following provides a more detailed explanation of the present invention through examples thereof, the present invention is not limited thereto.

<Adipose-Derived Mesenchymal Stem Cells>

Poietics adipose-derived mesenchymal stem cells (PT-5006, Lonza Group Ltd.) were used for the adipose-derived mesenchymal stem cells (AD-MSC).

<Human Corneal Epithelial Cells>

Human corneal epithelial cells (HCEC) were prepared in the manner indicated below. Human corneal epithelial cells were harvested from the limbus of an imported human cornea (SightLife, Wash.) and cultured to a density of 70% to 90% in an incubator set to an environment of 37° C. and 5% $CO_2$ using CnT-Prime Epithelial Cell Culture Medium (CnT-PR, CELLnTEC Advanced Cell Systems AG) in a 10 cm dish (353003, Falcon). After washing once with 10 ml of PBS (14190-144, Gibco Corp.), the cells were subjected to an enzyme reaction for 5 to 10 minutes using 2 ml of TrypLE Express (12605-010, Gibco Corp.) in an incubator set to 37° C. and 5% CO2 followed by the addition of 8 ml of PBS, centrifuging for 5 minutes at 1300 rpm with a centrifuge (LC-230, Tomy Co., Ltd.) and removing the supernatant. The pellet was suspended to $110^6$ cells/ml using Stem-Cell Banker (CB046, Nippon Zenyaku Kogyo Co., Ltd.) and stored in a freezer at 150° C. until the time of use.

Media

MSCGM-CD Bullet Kit (Ser. No. 00/190,632, Lonza Group Ltd.) was used for the medium for culturing AD-MSC and recovering exosomes.

DMEM, High Glucose, Pyruvate (11995-065, Gibco Corp.) containing 10% FBS and 1% Antibiotic-Antimycotic (15240-062, Gibco Corp.) was used as medium to culture NIH/3T3 cells.

In addition, CnT-Prime (CnT-PR, CELLnTEC Advanced Cell Systems AG) was used for expansion culturing of the HCEC used at colony assay, and KCM medium containing 5% FBS (Hayashi, Ryuhei, et al.: "Validation system of tissue-engineered epithelial cell sheets for corneal regenerative medicine", Tissue Engineering Part C: Methods 16.4 (2009): 553-560) was used as the medium during colony formation.

<Preparation of Exosomes>

1. Recovery of Culture Supernatant for Extracting Exosomes

AD-MSC (PT-5008, Lonza Group Ltd., passages: 4-6) were cultured in an incubator set to an environment of 37° C. and 5% $CO_2$ using 13 ml of MSCGM-CD at a density of 5000 cells/cm² in a T-75 flask (353136, Falcon). The medium was replaced with 13 ml of fresh MSCGM-CD when the cell density reached 70% to 90% followed by culturing for 3 more days in the same environment and recovering the culture supernatant for isolating exosomes. The culture supernatant was dispensed into a 15 ml tube (352096, Falcon) and stored at −80° C. until it is used to isolate exosomes.

2. Isolation of Exosomes by Ultracentrifugation

Ultracentrifugation was carried out as described in the report indicated below. The method referred to is shown in FIG. 1. (Thery, C., Amigorena, S., Raposo, G and Clayton, A. (2006): Isolation and characterization of exosomes from cell culture supernatants and biological fluids, Current Protocols in Cell Biology, Editorial Board: Juan S. Bonifacino, et al., Chapter 3, Unit 3.22, doi:10.1002/0471143030.cd0322s30).

The Hitachi CP80WX was used for the centrifuge, the PA90AT rotor was used, and a 10 PC bottle assembly (325952A, Hitachi, Ltd.) subjected to autoclaving treatment for 20 minutes at 121° C. was used for the ultracentrifugation tubes. After 8 ml of supernatant/tube was centrifuged for 10 minutes at 300 G at room temperature, the supernatant was recovered and the pellet comprised of live cells was removed followed by centrifuging for 10 minutes at 4° C. and 2,000 G, recovering 8 ml of supernatant and removing the pellet comprised of dead cells. This supernatant was further centrifuged for 30 minutes at 4° C. and 10,000 G followed by recovering 8 ml of supernatant and removing the pellet comprised of cell fragments and the like. Subsequently, the supernatant was transferred to an ultracentrifuge tube and ultracentrifuged for 70 minutes at 4° C. and 100,000 G followed by removing the supernatant to obtain a pellet comprised of exosomes, re-suspending the pellet with 8 ml of PBS, ultracentrifuging again for 70 minutes at 4° C. and 100,000 G, and removing the supernatant to ultimately obtain a pellet comprised of exosomes.

<Colony Formation Test>

1. Examination of Effects of Exosomes

NIH/3T3 cells, treated for 2 hours with Mitomycin C (Mitomycin for Injection, 2 mg, Kyowa Hakko Kirin Co., Ltd.) at 8 μg/ml in a 24-well plate (353047, Falcon), were disseminated using DMEM containing 10% FBS at 1×10⁴ cells/cm² for use as feeder cells. After removing the culture supernatant of HCEC (passage=2) cultured in a 10 cm dish until subconfluency and then washing with 10 ml of PBS, 2 ml of TrypLE Express (12605-010, Gibco Corp.) were added to carry out an enzyme reaction in an incubator set to an environment of 37° C. and 5% $CO_2$. The cells were added 8 ml of PBS, followed by transferring to a 15 ml tube, centrifuging for 15 minutes at room temperature and 1300 rpm with a centrifuge (LC-230, Tomy Co., Ltd.) to obtain an HCEC pellet. The pellet was suspended in KCM containing 5% FBS followed by disseminating onto the NIH/3T3 feeder cells at 200 cells/well. The amount of medium was made to be a total of 300 µl/well. The medium was replaced a total of three times at a frequency of once every 2 to 3 days, the exosomes were replaced with fresh exosomes each time, and culturing was continued for 10 days in the same environment. The exosomes were treated by adjusting with KCM medium containing 5% FBS to a concentration of 20 µg/ml or 30 µg/ml as the amount of protein measured by BCA assay.

2. Colony Assay (Staining)

The culture broth was washed once with 500 µl of PBS followed by the addition of 300 µl of 10% formaldehyde buffer and fixing for 2 hours or more at RT. Subsequently, the wells were washed once with 500 µl of ultrapure water, and after adding 300 µl of 2% Rhodamine B and allowing to react for 30 minutes or more at room temperature, the wells were washed one to three times with 0.2 M HCl and dried at room temperature followed by scanning the wells with a scanner (GT-F740, Epson Corp.) or photographing with EVOS FL AUTO (Thermo Fisher Scientific Inc.) to obtain images thereof (FIG. 2). Colonies were then counted based on these images. Colony-forming efficiency (CFE, %) was calculated using the formula: "100×no. of colonies/no. of disseminated cells". As shown in FIG. 3, CFE of the control cells was 5.6% while CFE of cells treated with exosomes was 9.1%, demonstrating that exosome-treatment significantly increased colony formation. On the basis of the above results, AD-MSC-derived exosomes were confirmed to have a colony formation promoting action on HCEC.

3. Analysis of Colony Area

The images of the wells incorporated with a scanner were analyzed using Image J 1.455 to obtain the value of the area of each colony. The results are shown in FIG. 4. The presence of exosomes was clearly determined to have the effect of increasing the size of individual colonies. On the basis thereof, exosomes were indicated to have activity that promotes cell growth of HCEC colonies.

4. Statistical Analyses

<Statistical Analyses>

Statistical analyses were carried out using R Version 3.11 and EZR Version 1.25.

<Colony Gene Expression Analysis>

1. K12 Gene Expression Analysis

After removing the culture supernatant and washing once with 500 µl of PBS, 1 ml of QIAzol Lysis Reagent (79306, Qiagen, Inc.) was added to each well of the resulting colonies followed by recovering total RNA, purifying the total RNA in accordance with the protocol, and carrying out a reverse transcriptase reaction using SuperScript III First-Strand Synthesis SuperMix for qRT-PCR (Ser. No. 18/080, 400, Thermo Fisher Scientific Inc.) to obtain cDNA. Applied Biosystems 7500 Fast was then used to carry out real-time PCR using GAPDH and K12 TaqMan® Gene Expression Assay (Hs99999905_m1 and Hs00165015_m1, respectively). The results were indicated as the relative amount versus the expressed amount of GAPDH using the comparative CT method. The results are shown in FIG. 5.

2. K12 Immunofluorescent Staining

The formed colonies were washed once with 500 µl of PBS and fixed at room temperature for 30 minutes with 300 µl of MeOH cooled to −30° C. Subsequently, after carrying out blocking for 1 hour at room temperature with 300 µl of 5% NST (5% normal donkey serum, 0.3% Triton/TBS), 300 µl of Cytokeratin 12 Antibody (N-16) (SC-17098, Santa Cruz Biotechnology, Inc.) which was diluted 100-fold with 1% NST (1% normal donky serum, 0.3% Triton/TBS) were added followed by treating for 3 hours at room temperature. After washing three times with 300 µl of PBS, 300 µl of donkey anti-goat IgG (H+L) secondary antibody, Alexa Fluor 647 Conjugate (A21447, Thermo Fisher Scientific Inc.), in 200-fold dilution was added, followed by treating for 1 hour at room temperature, after which the colonies were treated with Hoechst stain for the final 10 minutes to stain the nuclei. After washing three times with µl of PBS, 300 µl of PBS were added followed by photographing samples at a wavelength of 647 nm using a fluorescent inverted microscope (AxioObserver D1, Carl Zeiss AG). The results are shown in FIG. 6. On the basis of the above results, AD-MSC-derived exosomes were indicated to have an inhibitory effect on HCEC differentiation markers.

3. Analysis of Other Marker Genes

Analyses of K3, K14, K15, p63 (TP63), N-cadherin (CDH2) and PAX6 were carried out in accordance with the method used to analyze K12 gene expression. The following were used for the Taqman Gene Expression Assay: K3 (Hs00365080_m1), K12 (00165015_m1), K14 (Hs00559328_m1), K15 (Hs00267035 m1), p63 (Hs009778339_m1), N-cadherin (Hs00983056_m1) and PAX6 (Hs00240871_m1). The results are shown in FIG. 5. Although the expression of the corneal epithelial cell differentiation marker, K3, or PAX6, which plays an important role during differentiation, was inhibited, expression of corneal epithelial stem cell markers consisting of K14, KI5, p63 and N-cadherin was determined to increase. These results suggested that AD-MSC-derived exosomes have function that promotes colony formation by inhibiting differentiation of corneal epithelial stem cells and maintaining the corneal epithelial stems cells in an undifferentiated state.

<Exosome Proteome Analysis>

Shotgun Analysis of Proteins Present in Exosomes

An exosome pellet was obtained according to the previously described method. 2% sodium deoxycholate (190-08313, Wako Pure Chemical Industries, Ltd.) and 1× Protease Inhibitor Cocktail Set I (165-26021, Wako Pure Chemical Industries, Ltd.) added to 10 µl of 100 mM Tris-HCl (pH 8.0) were added to the exosome pellet followed by suspending therein by vortexing and then allowing to stand undisturbed at 4° C. and O/N. Protein was assayed with a BCA assay kit (Pierce, 23227) and 10 µl of protein diluted to 1 µg/ml was used in a shotgun analysis. QTRAP 5500 (AB Sciex) was used for analysis.

The aforementioned exosomes were confirmed to contain CD9, CD63, CD81, GAPDH, PKM, Enolase-1, 40S ribosomal protein S2, S5, SA, S13, S23, S4, S16 and S9, 60S acidic ribosomal protein PO and P1, 60S ribosomal protein L9, HSPB1 and HSP7C, 14-3-3 protein zeta/delta, epsilon, theta, beta/alpha, gamma and eta, syntenin, TGS101, actin cytoplasmic-1, cofilin-1, annexin A1, A2, A5, A6, A7 and A11, Rab-1B, 7a, 8B, 11A, 13 and 35, ICAM-1, and integrin alpha-V, alpha-2, alpha-4, alpha-5, beta-1 and beta-5.

<Evaluation of Exosome CD63 Expression Level by Western Blotting>

Using D10132 (Takara Bio Inc.) for bone marrow-derived mesenchymal stem cells (BM), KW-4009 (Kurabo) for umbilical cord-derived mesenchymal stem cells (UC), and KF-4009 (Kurabo) for normal human dermal fibroblasts (NHDF), exosomes were isolated from each culture supernatant thereof containing AD-MSC according to the previously described method. Exosomes obtained by carrying out the same treatment on MSCGM-CD without culturing the cells were used in a control (CTL) group. The exosome pellets were suspended using 10 µl of RIPA Lysis and Buffer (89900, Thermo Fisher Scientific Inc.) containing Protease Inhibitor Cocktail Set I (Wako Pure Chemical Industries, Ltd., 165-26021). The exosomes were homogenized by treating at 20% for 5 seconds using the QSONICA Q125 small sample ultrasonic homogenizer, and the supernatant was recovered by centrifuging for 15 minutes at 4° C. and 14,000 G. After assaying the protein in the supernatant with the BCA kit (Pierce, 23227), an amount of 4×NuPAGE LDS sample buffer (Bio-Rad Laboratories, Inc.) equal to one-fourth the sample volume was added to the sample, and after treating the sample with a heating block heated for 10 minutes at 70° C., 3 µg aliquots of the sample in terms of the amount of protein therein were applied to 4% to 12% NuPAGE Novex Bis-Tris gel (Invitrogen Corp.) followed by carrying out SDS-PAGE. After transferring to a PVDF membrane using the iBlot system (Invitrogen Corp.), blocking was carried out for 1 hour at room temperature in PBS containing 5% skim milk. After washing three times for 5 minutes with TBS containing 0.05% Tween 20 (TBS-T), it was allowed to react overnight with the primary antibody at 4° C., and after washing three times for 5 minutes with TBS-T, the membrane was allowed to react for 1 hour with the secondary antibody at room temperature. Anti-CD63 antibody (10628D, Thermo Fisher Scientific Inc., diluted 1:1000 (TBS)) was used for the primary antibody, and HRP-labeled anti-mouse IgG antibody (diluted 1:10,000 (PBS)) was used for the secondary antibody. ECL Prime (GE Healthcare Biosciences Corp.) was used for luminescence, and luminescence was detected with ChemiDoc XRS (Bio-Rad Laboratories, Inc.). AD-MSC-derived exosomes expressed CD63, and exosomes derived from UC-MSC (umbilical cord-derived mesenchymal stem cells) and BM-MSC (bone marrow-derived mesenchymal stem cells) also expressed CD63, albeit at lower levels than in the case of AD-MSC-derived exosomes. These results suggested that AD-MSC has a possibility to secrete more exosomes as compared to other cells.

INDUSTRIAL APPLICABILITY

The mesenchymal stem cell-derived microparticles of the present invention have industrial applicability since it has activity that promotes the growth of corneal epithelial stem cells and/or corneal epithelial cells, activity that maintains corneal epithelial stem cells in an undifferentiated state or promotes colony formation thereby, and action that protects corneal epithelium.

The invention claimed is:

1. A method for preventing and/or treating a corneal epithelial disease comprising:
recovering mesenchymal stem cell-derived isolated exosomes from a supernatant; and
using the recovered mesenchymal stem cell-derived isolated exosomes at a concentration of 20 µg/ml to 30 µg/ml as the amount of protein to prevent and/or treat the corneal epithelial disease, wherein the mesenchymal stem cell-derived isolated exosomes are derived from adipose tissue mesenchymal stem cells (AD-MSCs).

2. The method for preventing and/or treating a corneal epithelial disease according to claim 1, wherein the corneal epithelial disease is selected from the group consisting of heat corrosion, alkali corrosion, acid corrosion, chemical toxicity, Stevens-Johnson syndrome, ocular pemphigoid, (recurrent) pterygium, persistent corneal epithelial defect, corneal puncture, corneal marginal ulcer, corneal ulcer, epithelial detachment following excimer laser surgery, radiation keratopathy, aniridia, post-trachoma corneal opacification, Salzmann's corneal degeneration, corneal erosion, symblepharon, cryptogenic diseases associated with loss of corneal epithelial stem cells, limbus tumor, graft versus host disease (GVHD), keratitis, superficial punctate keratopathy, dry eye, keratoconjunctivitis sicca, corneal epithelial stem cell deficiency, corneal dystrophy, diabetic keratopathy and corneal epithelial disorders.

3. The method for preventing and/or treating a corneal epithelial disease according to claim 1, wherein the corneal epithelial disease is selected from the group consisting of corneal epithelial disorders, superficial punctate keratopathy, corneal erosion, corneal marginal ulcer, persistent corneal epithelial defect, dry eye, epithelial detachment following excimer laser surgery, heat corrosion, alkali corrosion, acid corrosion, chemical toxicity, diabetic keratopathy, corneal epithelial stem cell deficiency, Stevens-Johnson syndrome, ocular pemphigoid, aniridia, cryptogenic diseases associated with loss of corneal epithelial stem cells and graft versus host disease (GVHD).

4. The method for preventing and/or treating a corneal epithelial disease according to claim 1, wherein the corneal epithelial disease is selected from the group consisting of corneal epithelial disorders, superficial punctate keratopathy, corneal erosion, corneal marginal ulcer, persistent corneal epithelial defect, dry eye, epithelial detachment following excimer laser surgery, heat corrosion, alkali corrosion, acid corrosion, chemical toxicity and diabetic keratopathy.

5. The method for preventing and/or treating a corneal epithelial disease according to claim 3, wherein the corneal epithelial stem cell deficiency is caused by an extrinsic factor, an intrinsic factor, a congenital defect or a neoplastic disease.

6. The method for preventing and/or treating a corneal epithelial disease according to claim 1, wherein the mesenchymal stem cell-derived isolated exosomes are recovered by ultracentrifugation, density gradient centrifugation or an exosome separation kit and have activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium.

7. The method for preventing and/or treating a corneal epithelial disease according to claim 2, wherein the mesenchymal stem cell-derived isolated exosomes are recovered by ultracentrifugation, density gradient centrifugation or an exosome separation kit and have activity that promotes the growth of corneal epithelial stem cells and/or corneal epithelial cells, activity that maintains corneal epithelial stem cells in an undifferentiated state or promotes the formation of colonies by corneal epithelial stem cells, or function that protects corneal epithelium.

8. The method for preventing and/or treating a corneal epithelial disease according to claim 1, wherein the mesenchymal stem cell-derived isolated exosomes are recovered by ultracentrifugation, density gradient centrifugation or an exosome separation kit and have a density as determined by density gradient centrifugation of 1.13 g/mL to 1.19 g/m L.

9. The method for preventing and/or treating a corneal epithelial disease according to claim 2, wherein the mesenchymal stem cell-derived isolated exosomes are recovered by ultracentrifugation, density gradient centrifugation or an exosome separation kit and have a density as determined by density gradient centrifugation of 1.13 g/mL to 1.19 g/m L.

10. The method for preventing and/or treating a corneal epithelial disease according to claim 1, wherein the mesenchymal stem cell-derived isolated exosomes are recovered by ultracentrifugation, density gradient centrifugation or an exosome separation kit.

11. The method for preventing and/or treating a corneal epithelial disease according to claim 2, wherein the mesenchymal stem cell-derived isolated exosomes are recovered by ultracentrifugation, density gradient centrifugation or an exosome separation kit.

12. The method for preventing and/or treating a corneal epithelial disease according to claim 1, wherein the mesenchymal stem cell-derived isolated exosomes are recovered by ultracentrifugation, density gradient centrifugation or an exosome separation kit and comprise one or more of CD9; CD63; CD81; GAPDH; PKM; Enolase-1; 40S ribosomal protein S2, S5, SA, S13, S23, S4, S16 and/or S9; 60S acidic ribosomal protein PO and/or P1; 60S ribosomal protein L9, HSPB1 and/or HSP7C; 14-3-3 protein zeta/delta, epsilon, theta, beta/alpha, gamma and/or eta; syntenin; TGS101; actin cytoplasmic-1; cofilin-1; annexin A1, A2, A5, A6, A7 and/or A11; Rab-1B, 7a, 8B, 11A, 13 and/or 35; ICAM-1; and/or integrin alpha-V, alpha-2, alpha-4, alpha-5, beta-1 and/or beta-5.

13. The method for preventing and/or treating a corneal epithelial disease according to claim 2, wherein the mesenchymal stem cell-derived isolated exosomes are recovered by ultracentrifugation, density gradient centrifugation or an exosome separation kit and comprise one or more of CD9; CD63; CD81; GAPDH; PKM; Enolase-1; 40S ribosomal protein S2, S5, SA, S13, S23, S4, S16 and/or S9; 60S acidic ribosomal protein PO and/or P1; 60S ribosomal protein L9, HSPB1 and/or HSP7C; 14-3-3 protein zeta/delta, epsilon, theta, beta/alpha, gamma and/or eta; syntenin; TGS101; actin cytoplasmic-1; cofilin-1; annexin A1, A2, A5, A6, A7 and/or A11; Rab-1B, 7a, 8B, 11A, 13 and/or 35; ICAM-1; and/or integrin alpha-V, alpha-2, alpha-4, alpha-5, beta-1 and/or beta-5.

14. The method for preventing and/or treating a corneal epithelial disease according to claim 1, wherein the mesenchymal stem cell-derived isolated exosomes are recovered by ultracentrifugation, density gradient centrifugation or an exosome separation kit and comprise one or more of CD9; CD63 and/or CD81.

15. The method for preventing and/or treating a corneal epithelial disease according to claim 2, wherein the mesenchymal stem cell-derived isolated exosomes are recovered by ultracentrifugation, density gradient centrifugation or an exosome separation kit and comprise one or more of CD9; CD63; and/or CD81.

16. The method for preventing and/or treating a corneal epithelial disease according to claim 1, wherein the mesenchymal stem cell-derived isolated exosomes are recovered by ultracentrifugation, density gradient centrifugation or an exosome separation kit, and the using the mesenchymal stem cell-derived isolated exosomes comprises using the mesenchymal stem cell-derived isolated exosomes in a dosage of the mesenchymal stem cell-derived isolated exosomes of 100 pg/kg to 10 mg/kg per day.

17. The method for preventing and/or treating a corneal epithelial disease according to claim 2, wherein the mesenchymal stem cell-derived isolated exosomes are recovered by ultracentrifugation, density gradient centrifugation or an exosome separation kit, and the using the mesenchymal stem-cell derived isolated exosomes comprises using the mesenchymal stem cell-derived isolated exosomes in a dosage of the mesenchymal stem cell-derived isolated exosomes of 100 pg/kg to 10 mg/kg per day.

\* \* \* \* \*

UNITED STATES PATENT AND TRADEMARK OFFICE
CERTIFICATE OF CORRECTION

PATENT NO. : 11,357,798 B2
APPLICATION NO. : 15/749766
DATED : June 14, 2022
INVENTOR(S) : Kohji Nishida et al.

Page 1 of 1

It is certified that error appears in the above-identified patent and that said Letters Patent is hereby corrected as shown below:

In the Claims

Column 20, Line 34, Claim 17  Delete "stem-cell derived" and
Insert -- stem cell-derived --

Signed and Sealed this
Twenty-seventh Day of June, 2023

Katherine Kelly Vidal
*Director of the United States Patent and Trademark Office*